(12) United States Patent
Draper et al.

(10) Patent No.: US 11,975,108 B2
(45) Date of Patent: *May 7, 2024

(54) PHARMACEUTICAL FORMULATIONS OF STATINS AND OMEGA-3 FATTY ACIDS FOR ENCAPSULATION

(75) Inventors: Peter Draper, Amherstburg (CA); James Draper, Lasalle (CA); Beth Marie Okutan, London (CA)

(73) Assignee: Catalent Ontario Limited, Windsor (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/701,463

(22) PCT Filed: Jun. 3, 2011

(86) PCT No.: PCT/CA2011/000650
§ 371 (c)(1),
(2), (4) Date: Jan. 18, 2013

(87) PCT Pub. No.: WO2011/150505
PCT Pub. Date: Dec. 8, 2011

(65) Prior Publication Data
US 2013/0115281 A1 May 9, 2013

(30) Foreign Application Priority Data
Jun. 3, 2010 (CA) .................................. CA 2706270

(51) Int. Cl.
*A61K 9/50* (2006.01)
(52) U.S. Cl.
CPC ................... *A61K 9/5084* (2013.01)

(58) Field of Classification Search
CPC ....................................................... A61K 9/5084
(Continued)

(56) References Cited

U.S. PATENT DOCUMENTS

| 2,775,080 A | 12/1956 | Stirn et al. |
| 3,536,074 A | 10/1970 | Aufhauser |

(Continued)

FOREIGN PATENT DOCUMENTS

| CA | 2512988 A1 | 8/2004 |
| CA | 2475765 A1 | 1/2005 |

(Continued)

OTHER PUBLICATIONS

Chung et al. ("Bioavailability of Amlodipine Besylate/Atorvastatin Calcium Combination Tablet" in The Journal of Clinical Pharmacology, vol. 46, Issue 9, 2006, 1030-1037).*

(Continued)

*Primary Examiner* — Blessing M Fubara
(74) *Attorney, Agent, or Firm* — LOWENSTEIN SANDLER LLP

(57) ABSTRACT

A multi phase soft gelatin dosage form comprising at least one preformed solid dosage form comprising a statin compound and at least one liquid fill phase comprising Omega-3 fatty acids. The multi phase soft gelatin dosage forms of the present invention are especially useful to combine at least one solid dosage form and at least one liquid phase for single ingestion. The solid phase, liquid phase or coatings may further comprise active pharmaceutical ingredients, nutraceuticals, nutritional supplements, or therapeutic substances, functional excipients or combinations thereof.

11 Claims, 1 Drawing Sheet

(58) Field of Classification Search
USPC .................. 424/452; 514/275, 419, 423, 548
See application file for complete search history.

(56) References Cited

U.S. PATENT DOCUMENTS

| | | | |
|---|---|---|---|
| 4,655,027 A | 4/1987 | Chasman | |
| 6,238,616 B1 | 5/2001 | Ishikawa | |
| 2002/0134055 A1 | 9/2002 | Martinez | |
| 2004/0146537 A1* | 7/2004 | Radhakrishnan | A61K 9/4858 424/400 |
| 2006/0003947 A1* | 1/2006 | Udell | A61K 9/4858 514/26 |
| 2007/0191467 A1* | 8/2007 | Rongen | A61P 3/06 514/460 |
| 2007/0218141 A1* | 9/2007 | Mehta | A61K 9/14 424/489 |
| 2007/0276027 A1* | 11/2007 | Campeta | C07D 207/34 514/423 |
| 2008/0292720 A1* | 11/2008 | Darlington, Jr. | A61K 31/19 424/600 |
| 2009/0208568 A1* | 8/2009 | Hannetel et al. | 424/452 |
| 2010/0062057 A1* | 3/2010 | Berge et al. | 424/455 |
| 2011/0268770 A1* | 11/2011 | Seternes | A61K 9/0056 424/400 |

FOREIGN PATENT DOCUMENTS

| | | | |
|---|---|---|---|
| CA | 2 711 814 | * | 7/2009 |
| CA | 2 711 814 A1 | * | 7/2009 |
| CA | 2711814 A1 | | 7/2009 |
| EP | 1 803 440 A1 | * | 4/2007 |
| EP | 1 803 440 A1 | * | 7/2007 |
| EP | 1803440 A1 | | 7/2007 |
| WO | 1995/000125 A1 | | 1/1995 |
| WO | WO 2004066925 A3 | * | 8/2004 |
| WO | 2008/000731 A2 | | 1/2008 |
| WO | 2010/041017 A2 | | 4/2010 |

OTHER PUBLICATIONS

Lipitor 10 mg film coated tablets, authorisation in Sep. 8, 1997, Renewal 2013 (Year: 1997).*
Crestor 5 mg film coated tablets, authorisation/renewal Nov. 6, 2012 (Year: 2012).*
Crestor, Product Brochure Feb. 26, 2007 (Year: 2007).*
Lipitor, product Brochure, Approval 1996 (Year: 1996).*
Rampurna Prasad Gullapalli's review article, Soft Gelatin Capsules (Softgels), in the Journal of Pharmaceutical Sciences, vol. 99, No. 10, Oct. 2010, pp. 4107-4148. (Year: 2010).*
Yokoyama et al., "Effects of eicosapaentaenoic acid on major coronary events in hypercholesterolaemic patients (JELIS): a randomised opne-label, blinded endpoint analysis" in Lancet, 2007, 369, pp. 1090-1098. (Year: 2007).*
International Search Report and Written Opinion of PCT/CA2011/000650 mail dated Sep. 13, 2011.
European Communication dated Mar. 26, 2015, issued in Application No. EP 11 78 9015.2-1651/2575788.
Australian Patent Examination Report No. 1, issued Aug. 3, 2014 in Application No. 2011261117.
Matsuzaki M et al. "Incremental effects of eicosapentaenoic acid on cardiovascular events in statin-treated patients with coronary artery disease" Circ J. 2009;73(7):1283-90. Epub May 8, 2009.
Singh MN et al. "Microencapsulation: A promising technique for controlled drug delivery" Res Pharm Sci. 2010;5 (2):65-77.

* cited by examiner

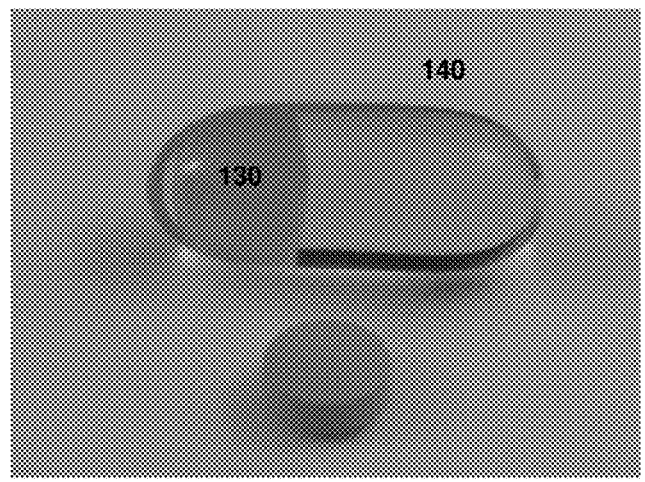

PHARMACEUTICAL FORMULATIONS OF STATINS AND OMEGA-3 FATTY ACIDS FOR ENCAPSULATION

FIELD OF THE INVENTION

The present invention generally relates to soft gelatin dosage forms for oral administration comprising multiple phases. More particularly, the present invention relates to pharmaceutical compositions in unit dose form comprising soft gelatin capsules containing an oil phase and at least one HMG-CoA reductase inhibitor in solid form within the oil phase.

BACKGROUND OF THE INVENTION

Statins are a class of drugs for the treatment of hypercholesterolemia and hyperlipidemia, which are known risk factors for arthrosclerosis and coronary heart disease. It is well known that statins inhibit the enzyme the 3-hydroxy-3-methyglutaryl coenzyme A (HMG-CoA) reductase that forms cholesterol in the liver. The administration of statins or HMG-CoA reductase inhibitors has been shown to lower cholesterol levels.

Statins can be found in acid form or lactone form. It is generally known that statins become unstable when exposed to heat, moisture, low pH and light. For example, statins are susceptible to interconversion between their hydroxy acid and lactone forms in an acidic environment. Acid forms may also be converted to lactone forms through hydrolysis.

It is well known that one form may provide better inhibition of the biosynthesis of cholesterol than the other. Thus, interconversion of statin compounds between hydroxy acid and lactone forms is undesirable. Due to the instability of statins, it is desirable to provide stable formulations of statins to avoid degradation or interconversion. Tablet compositions of statin compounds address stability problems by incorporating anhydrous and alkaline excipients. Further, statin tablets are typically film-coated with a cellulose derivative or similar coating to provide a moisture barrier.

Commercially available statin compounds are in tablet dosage form and include LIPITOR™ or TORVAST™ (atorvastatin calcium) sold by Pfizer, LESCOL™ or LESCOL XL™ (fluvastatin sodium) sold by Novartis, MEVACOR™, ALTOCORT™ or ALTOPREV™ (lovastatin) sold by Merck, LIVALO™ or PITAVA™ (pitavastatin) sold by Kowa, PRAVACHOL™, SELEKTINE™ or LIPOSTAT™ (pravastatin sodium) sold by Bristol Myers Squibb, CRESTOR™ (rosuvastatin calcium) sold by AstraZeneca, and ZOCOR™ or LIPEX™ (simvastatin) sold by Merck. Examples of established tablet dosage forms containing statin compounds with an additional active ingredient include VYORTIN™ (simvastatin and exetimibe) sold by Merck, ADVICOR™ (lovastatin and niacin) sold by Merck, CADUET™ (atorvastatin calcium and amlodipine besylate) sold by Pfizer, and SIMCOR™ (simvastatin and niacin) sold by Merck.

The incorporation of statin compounds in soft gelatin fill formulations has additional challenges. Statin compounds formulated in a liquid fill formulation are highly susceptible to interconversion due to moisture and pH. Statin compounds are also incompatible with most common soft gelatin fill ingredients and shell ingredients. Thus, due to stability and incompatibility problems, statin compounds are not suitable for formulation in soft gelatin dosage forms.

Omega-3 fatty acids are well known to help reduce risk factors for heart disease, including high cholesterol and high blood pressure. Omega-3 fatty acids are often administered as part of a standard treatment for patients with high cholesterol. Omega-3 fatty acids are typically formulated in soft gelatin capsule dosage forms.

A common drug regimen for high cholesterol includes combined administration of statins and a high potency omega-3 oil, such as Lovaza™ by GlaxoSmithKline. The statins and omega-3 oils are administered as separate single dosage forms.

The ability to incorporate a statin and omega-3 oil in a single dosage form offers several advantages. The advantages include convenient delivery of multiple medications, avoidance of potential mistakes by user if many medications are to be taken in a single day, increased user compliance, possible synergistic effect and possible controlled delivery.

Attempts have been made to combine a statin and omega-3 oil in a single dosage form. In United States Patent Application Publication No. 2007/0212411 to Fawzy, coated soft gelatin capsules are disclosed. In particular, omega-3 oils are contained within soft gelatin capsules. The capsules may be coated with a coating comprising a statin mixed with a coating material. Since the statins must be mixed with a coating material and then sprayed on the capsule to form a coating, the established pharmaceutical characteristics, active ingredient release profile, bioavailability and clinical performance of the statins are not retained. Further, in Fawzy, complicated processing steps are required to obtain the statin and omega-3 oil in a single dosage form.

There exists a need for soft gelatin dosage forms containing a statin compound in solid dosage form and omega-3 oil fill phase which maintains the chemical stability of each phase and prevents any chemical reaction between the multiple phases. It is desirable to incorporate preformed solid dosage forms to retain the established pharmaceutical characteristics of the preformed solid dosage form in combination with a liquid phase, such as physical and chemical stability, active ingredient release profile of the solid dosage form, bioavailability and clinical performance.

SUMMARY OF THE INVENTION

In accordance with an aspect of the present invention, there is provided multi phase soft gelatin dosage forms containing at least one liquid phase comprising an Omega-3 oil and at least one solid phase comprising a statin compound.

It is a further aspect of the present invention to produce soft gelatin dosage forms which provide single ingestion of multiple dosage forms, each having different phases.

The invention further provides soft gelatin dosage forms containing a solid dosage form and liquid fill phase which maintains the chemical stability of each phases and prevents any chemical reaction between the multiple phases.

It is a further aspect of the present invention to incorporate preformed solid dosage forms within soft gelatin dosage forms. This capability retains the established pharmaceutical characteristics of the preformed solid dosage form in combination with a liquid phase, such as physical and chemical stability, active ingredient release profile of the solid dosage form, bioavailability and clinical performance.

In accordance with an aspect of the present invention, there is provided a multi phase soft gelatin capsule for oral administration comprising at least one preformed solid dosage form comprising a statin compound and at least one liquid fill phase comprising omega-3 fatty acids. The at least one solid dosage form and the at least one liquid fill phase are independently introduced in the soft gelatin capsule.

In an embodiment of the present invention, there is a soft gelatin capsule as defined above, wherein the at least one preformed solid dosage form is a pharmaceutical grade finished dosage form.

In an embodiment of the present invention, there is a soft gelatin capsule as defined above, wherein the at least one preformed solid dosage form is selected from the group consisting of a tablet, a caplet, a capsule, a slug of solid material and a granule.

In another embodiment of the present invention, there is a soft gelatin capsule as defined above, wherein the at least one liquid fill phase further comprises at least one additional active ingredient.

In another embodiment of the present invention, there is a soft gelatin capsule as defined above, wherein the at least one additional active ingredient in the at least one liquid fill phase is selected from the group consisting of: an active pharmaceutical ingredient, nutraceutical, nutritional supplement, therapeutic substance, functional excipients and combinations thereof.

In another embodiment of the present invention, there is a soft gelatin capsule as defined above, wherein the at least one liquid fill phase further comprises diluent oils.

In another embodiment of the present invention, there is a soft gelatin capsule as defined above, wherein the diluent oils comprise vegetable oils, mineral oils, food grade oils, pharmaceutically acceptable oils or mixtures thereof.

In another embodiment of the present invention, there is a soft gelatin capsule as defined above, wherein the statin compound is selected from the group consisting of: atorvastatin, fluvastatin, lovastatin, pitavastatin, pravastatin, rosuvastatin, simvastatin and pharmaceutically acceptable salts thereof.

In another embodiment of the present invention, there is a soft gelatin capsule as defined above, wherein the statin compound is atorvastatin calcium.

In another embodiment of the present invention, there is a soft gelatin capsule as defined above, wherein the statin compound is fluvastatin sodium.

In another embodiment of the present invention, there is a soft gelatin capsule as defined above, wherein the statin compound is pravastatin sodium.

In another embodiment of the present invention, there is a soft gelatin capsule as defined above, wherein the statin compound is rosuvastatin calcium.

In another embodiment of the present invention, there is a soft gelatin capsule as defined above, wherein the statin compound further comprises at least one additional active ingredient.

In another embodiment of the present invention, there is a soft gelatin capsule as defined above, wherein the at least one additional active ingredient of the statin compound is an active pharmaceutical ingredient.

In another embodiment of the present invention, there is a soft gelatin capsule as defined above, wherein the statin compound is simvastatin and the at least one additional active ingredient is exetimibe.

In another embodiment of the present invention, there is a soft gelatin capsule as defined above, wherein the statin compound is lovastatin and the at least one additional active ingredient is niacin.

In another embodiment of the present invention, there is a soft gelatin capsule as defined above, wherein the statin compound is atorvastatin calcium and the at least one additional active ingredient is amlodipine besylate.

In another embodiment of the present invention, there is a soft gelatin capsule as defined above, wherein the statin compound is simvastatin and the at least one additional active ingredient is niacin.

In another embodiment of the present invention, there is a soft gelatin capsule as defined above, wherein the at least one preformed solid dosage form has at least one coating.

In another embodiment of the present invention, there is a soft gelatin capsule as defined above, wherein the at least one coating on the at least one preformed solid dosage form is selected from the group consisting of: immediate release coatings, protective coatings, enteric or delayed release coatings, sustained release coating, barrier coatings, moisture shield coatings, and combinations thereof.

In another embodiment of the present invention, there is a soft gelatin capsule as defined above, wherein the at least one coating on the at least one preformed solid dosage form is selected from the group consisting of: film coating, gelatin coating, and combinations thereof.

In another embodiment of the present invention, there is a soft gelatin capsule as defined above, wherein the at least one coating on the at least one preformed solid dosage form further comprises at least one active ingredient.

In another embodiment of the present invention, there is a soft gelatin capsule as defined above, wherein the at least one active ingredient of the at least one coating on the at least one preformed solid dosage form is selected from the group consisting of: an active pharmaceutical ingredient, nutraceutical, nutritional supplement, therapeutic substance, functional excipients and combinations thereof.

In another embodiment of the present invention, there is a soft gelatin capsule as defined above, wherein the omega-3 fatty acids comprise triglycerides, ethyl esters or an emulsified formulation of the omega-3 fatty acids.

In another embodiment of the present invention, there is a soft gelatin capsule as defined above, wherein the omega-3 fatty acids comprise eicosapentaenoic acid (EPA), docosahexaenoic acid (DHA), or a mixture thereof.

In another embodiment of the present invention, there is a soft gelatin capsule as defined above, wherein the soft gelatin capsule has at least one coating.

In another embodiment of the present invention, there is a soft gelatin capsule as defined above, wherein the at least one coating on the soft gelatin capsule is selected from the group consisting of: immediate release coatings, protective coatings, enteric or delayed release coatings, sustained release coating, barrier coatings, and combinations thereof.

In another embodiment of the present invention, there is a soft gelatin capsule as defined above, wherein the at least one coating on the soft gelatin capsule further comprises at least one active ingredient.

In another embodiment of the present invention, there is a soft gelatin capsule as defined above, wherein the at least one active ingredient of the at least one coating on the soft gelatin capsule is selected from the group consisting of: an active pharmaceutical ingredient, nutraceutical, nutritional supplement, therapeutic substance, functional excipients and combinations thereof.

BRIEF DESCRIPTION OF THE DRAWINGS

FIG. 1 is a perspective view of soft gelatin capsules according to the invention.

DETAILED DESCRIPTION

The present invention provides a soft gelatin capsule containing a solid phase comprising a statin and at least one oil phase. The solid phase and one or more liquid phases are encapsulated within a soft gelatin capsule. A soft gelatin dosage form is provided for the combined administration of unit doses of statin compounds or statin compounds in combination with other active ingredients and omega-3 fatty acids. Established unit dosage forms of the statin compounds include tablets or capsules containing single ingredient statins or statins in combination with other active ingredients.

The soft gelatin dosage forms of the present invention are capable of delivering multiple medications or therapeutic substances in a single dose, and provide the capabilities for engineering of pharmaceutical drug delivery systems providing differential release of medications or therapeutic substances from each phase. The multi phase soft gelatin dosage forms of the present invention are especially useful to combine two or more phases for single ingestion, where at least one is a solid phase and at least another is a liquid phase. The incorporation of a preformed solid dosage form into a soft gelatin capsule permits retention of the established pharmaceutical characteristics of the solid dosage form.

The solid phase may be in the form of preformed tablets, caplets, capsules, slugs of solid materials, granules or other solid dosage forms. Preferably, the solid phase is comprised of a preformed solid dosage form. More preferably, the preformed solid dosage form is a pharmaceutical finished dosage form, which is a dosage form suitable for administration to a human or animal subject, the pharmaceutical characteristics of which is acceptable and may be approved by regulatory authorities previously or subject to assessment by regulatory agencies.

The solid phase may consist of a single active ingredient statin compound or a combination of a statin compound and another active pharmaceutical ingredient. Statin compounds include, but are not limited to, atorvastatin, fluvastatin, lovastatin, pitavastatin, pravastatin, rosuvastatin, simvastatin and pharmaceutically acceptable salts thereof.

Commercially available single active ingredient statin compounds include LIPITOR™ or TORVAST™ (atorvastatin calcium) sold by Pfizer, LESCOL™ or LESCOL XL™ (fluvastatin sodium) sold by Novartis, MEVACOR™, ALTOCOR™ or ALTOPREV™ (lovastatin) sold by Merck, LIVALO™ or PITAVA™ (pitavastatin) sold by Kowa, PRAVACHOL™, SELEKTINE™ or LIPOSTAT™ (pravastatin sodium) sold by Bristol Myers Squibb, CRESTOR™ (rosuvastatin calcium) sold by AstraZeneca, ZOCOR™ and LIPEX™ (simvastatin) sold by Merck. These commercially available statin compounds are sold as film-coated tablets.

The solid phase of the present invention may include a solid dosage form comprising a combination of a statin compound and another active pharmaceutical ingredient. For example, commercially available statin combination products include, but are not limited to, VYORTIN™ (simvastatin and exetimibe) sold by Merck, ADVICOR™ (lovatatin and niacin) sold by Merck, CADUET™ (atorvastatin calcium and amlodipine besylate) sold by Pfizer, and SIMCOR™ (simvastatin and niacin) sold by Merck. These commercially available statin combination products are sold as film-coated tablets.

The shape and size of the solid dosage form can vary in accordance with the invention. The shape of the capsule may be, but is not limited to, round, oval, oblong, or a non-standard shape. The solid dosage form is sized to be less than the total internal volume of the soft gelatin capsule.

The solid dosage form may be coated with one or more coatings, including but not limited to, immediate release coatings, protective coatings, enteric or delayed release coatings, sustained release coatings, barrier coatings, moisture shield coatings and combinations thereof. The one or more coatings on the solid dosage form are useful to provide controlled release of an active ingredient in the solid dosage form, protect the solid dosage form from interactions with the liquid fill phase, or deliver one or more active ingredients. Preferably, the solid dosage form is film coated. The one or more coatings on the solid dosage form may be applied by any conventional coating technique recognized in the pharmaceutical industry, including but not limited to, pan coating, fluid bed coating or spray coating. Optionally, the coated or uncoated solid dosage form may be enrobed in gelatin film according to well known conventional tablet enrobing techniques.

Typical immediate release coating films are hydro-alcoholic film coatings or cellulose film coating systems as used in various pharmaceutical solid oral dosage forms. Typical coating systems may be aqueous, alcohol or organic solvent based or combinations containing hydroxy-propyl-methyl cellulose and derivatives, and polyvinyl alcohol and derivatives.

Typical protective coatings may include, but is not limited to, antioxidants, chelating agents, colours or dyes.

Typical enteric or delayed release coatings of the solid dosage form may consist of, but is not limited to, one or more of the following recognized coating agents: methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate/alginic acid and stearic acid.

Sustained release tablets may be film coated, enteric coated, or polymer matrix formulated. Sustained release film coatings may include, but is not limited to, a water insoluble material such as a wax or wax-like substance, fatty alcohols, shellac, zein, hydrogenated vegetable oils, water insoluble celluloses, polymers of acrylic and/or methacrylic acid, and any other slowly digestible or dispersible solids known in the art.

Moisture shield coatings provide moisture barriers for moisture sensitive or hygroscopic drugs. Such coatings may be applied to solid dosage forms to protect the solid dosage form moisture resulting from, for example, the soft gelatin encapsulation process of which utilizes water as a processing aid and primary plasticizer of the gelatin or functional polymer capsule shell system. The present invention may incorporate the solid dosage form coated with a suitable coating such as gelatin or other polymer to enhance the barrier properties of the solid in the liquid phase. Examples of dosage forms incorporating moisture shield coatings include, but are not limited to, atorvastatin calcium.

The liquid fill phase of the soft gelatin capsule is lipophilic and comprises one or more oils for carrying the solid dosage form that are compatible with the soft gelatin shell and do not interfere with or degrade the solid dosage form. The lipophilic liquid fill phase may be a therapeutic oil, an oil form of an active ingredient, an active ingredient or multiple active ingredient preparation that may be solutions, suspensions, emulsions, micro-emulsions, self-emulsifying systems, and other liquids that will be known to those who are expert in the field of soft gelatin capsules formulation. Examples of useful oils include omega-3 fatty acids, vegetable oils, mineral oils, other food grade oils and other pharmaceutically acceptable oils. Vegetable oils may include, but are not limited to, castor bean oil, coconut oil, peanut oil, palm kernel oil, canola oil, avocado oil, evening primrose oil, rice bran oil, borage oil, sunflower oil, soybean oil, palm oil, corn oil, olive oil, pumpkin seed oil, grape seed oil, sesame oil, argan oil and safflower oil. Preferred oils are omega-3 fatty acid triglycerides, omega-3 fatty acid ethyl esters, or an emulsified formulation of the omega-3 fatty acids. Examples of omega-3 fatty acids include alpha-linolenic acid, eicosapentaenoic acid (EPA) and docosa-hexaenoic acid (DHA). The omega-3 fatty acids may be a refined combination of EPA and DHA derived from natural sources such as fish or algae, or a purified form of EPA or DHA. Diluent oils may include vegetable oils, mineral oils, other food grade oils and other pharmaceutically acceptable oils.

The fill materials may also include excipients known in the art of soft gelatin encapsulation such as dispersants, surfactants, plasticizers, flavoring agents, opacifying agents, preservatives, embrittlement inhibiting agents, colorants, dyes and pigments, and disintegrants.

The fill formulation may be prepared using established procedures employed for manufacture of pharmaceutical solutions, suspensions and semi-solids, and recognized by those experts in the field of soft gelatin formulation.

The liquid phase or coating may also contain one or more active ingredients. The solid dosage form may comprise a combination of a statin compound and another active pharmaceutical ingredient. The present invention contemplates the use of any active ingredients known in the art. It is well within the knowledge of a skilled person in the art to select a particular combination of active ingredients or medicaments. In some embodiments, active ingredients may include, but are not limited to, the following: APIs, nutraceuticals, nutritional supplements, therapeutic substances, and functional excipients.

APIs may include, but are not limited to, the following: analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-pyretics anti-thyroid agents, anti-tussives, anxiolytics, sedatives, hypnotics, neuroleptics, neuroprotective agents, beta-blockers, cardiac inotropic agents, cell adhesion inhibitors, corticosteroids, cytokine receptor activity modulators, diuretics, anti-Parkinson's agents, gastrointestinal agents, histamine H-receptor antagonists, HMG-CoA reductase inhibitors, keratolytics, lipid regulating agents, muscle relaxants, nitrates and other anti-anginal agents, non-steroid anti-asthma agents, nutritional agents, opioid analgesics, sex hormones, stimulants, and anti-erectile dysfunction agents.

Nutraceuticals may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin B12), dimethylaminoethanol, fumaric acid, germanium sequioxide, glandular products, glucosamine HCl, glucosamine sulfate, hydroxylmethyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosyl-methionine, selenium yeast, shark cartilage, theobromine, vanadyl sulfate, and yeast.

Nutritional supplements may include vitamins, minerals, fiber, fatty acids, amino acids, herbal supplements or a combination thereof.

Vitamins may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Herbal supplements may include, but are not limited to, the following: arnica, bilberry, black cohosh, cat's claw, chamomile, echinacea, evening primrose oil, fenugreek, flaxseed, feverfew, garlic, ginger root, ginko biloba, ginseng, goldenrod, hawthorn, kava-kava, licorice, milk thistle, psyllium, rauowolfia, senna, soybean, St. John's wort, saw palmetto, turmeric, valerian.

Minerals may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Preferred nutritional supplements include, but are not limited to, the following: B vitamins and Vitamin B complex, beta-carotene, calcium, collagen, Co-Q-10, cranberry, echinacea, flax seed oil, folic acid, garlic, ginger, ginseng, glucosamine, chondroitin, green tea, iron, lecithin, lutein, lycopene, magnesium, melatonin, milk thistle, niacin, Omega-3 oils, potassium, probiotics, saw palmetto, selenium, St John's wort, tocopherols, valerian, vitamin A, vitamin B12, vitamin C, vitamin D, vitamin E, zinc and combinations thereof. Preferred nutritional supplement combinations include: Co-Q-10 and Omega-3 oils; echinacea, garlic and ginger; glucosamine and chondroitin; vitamin D and calcium; vitamin D, calcium and magnesium; vitamin D, calcium, magnesium and zinc; and vitamin E and other tocopherols.

The shape and size of the soft gelatin capsules can vary in accordance with the invention. The shape of the capsule may be, but is not limited to, round, oval, oblong, or a non-standard shape. Typical soft gelatin dosage form shapes and sizes may be, but are not limited to, those as shown in Table 1. The invention provides the capability to incorporate into the soft gelatin capsule a wide range of solid dosage components (form and shape) to manufacture an infinite variety of soft gelatin capsule shapes and sizes.

TABLE 1

Nominal Soft Gelatin Capsule Shapes and Sizes

| Nominal Size | Oblong Shape | | Oval Shape | |
|---|---|---|---|---|
| | Minimum Volume/ml | Maximum Volume/ml | Minimum Volume/ml | Maximum Volume/ml |
| 1 | 0.03 | 0.08 | 0.03 | 0.06 |
| 2 | 0.08 | 0.14 | 0.06 | 0.09 |
| 3 | 0.14 | 0.20 | 0.11 | 0.17 |
| 4 | 0.20 | 0.30 | 0.15 | 0.22 |
| 5 | 0.26 | 0.37 | 0.23 | 0.30 |
| 6 | 0.32 | 0.46 | 0.26 | 0.38 |
| 8 | 0.43 | 0.63 | 0.33 | 0.48 |
| 10 | 0.53 | 0.76 | 0.42 | 0.60 |
| 12 | 0.64 | 0.93 | 0.50 | 0.73 |

TABLE 1-continued

Nominal Soft Gelatin Capsule Shapes and Sizes

| Nominal Size | Oblong Shape | | Oval Shape | |
|---|---|---|---|---|
| | Minimum Volume/ml | Maximum Volume/ml | Minimum Volume/ml | Maximum Volume/ml |
| 14 | 0.75 | 1.06 | 0.60 | 0.85 |
| 16 | 0.85 | 1.23 | 0.70 | 1.00 |
| 18 | 0.96 | 1.40 | 0.76 | 1.10 |
| 20 | 1.10 | 1.55 | 0.85 | 1.20 |
| 22 | 1.20 | 1.70 | 0.95 | 1.35 |
| 24 | 1.30 | 1.85 | 1.05 | 1.46 |
| 26 | 1.40 | 2.00 | 1.13 | 1.60 |
| 28 | 1.50 | 2.15 | 1.23 | 1.70 |
| 30 | 1.65 | 2.30 | 1.30 | 1.85 |

The shell of the soft gelatin capsule may be formed from plasticized gelatin or other functional polymeric materials that are typically used for encapsulation of liquids, fluids, pastes or other fill materials.

The outer shell of the soft gelatin capsule may be coated with one or more coatings, including but not limited to, immediate release coatings, protective coatings, enteric or delayed release coatings, sustained release coating, barrier coatings, and combinations thereof. The one or more coatings on the outer shell of the soft gelatin capsule may be useful to provide controlled release of the soft gelatin capsule, protect the soft gelatin shell from degradation, or deliver one or more active ingredients which may be the same or different as those in the liquid phase and solid dosage form. Alternatively, additives such as pectin or synthetic polymers may be incorporated into the soft gelatin capsule shell to slow the dissolution on ingestion. Such coatings or additives to the soft gelatin shell phase are well described in the literature and known to those experts in the field. The one or more coatings outer shell of the soft gelatin capsule may be applied by any conventional technique, including but not limited to, pan coating, fluid bed coating or spray coating.

The soft gelatin capsules of the present invention may be prepared in accordance with the following methods. An apparatus such as disclosed in Canadian Patent Application No. 2,706,272 may be utilized to manufacture the soft gelatin capsule of the present invention.

An embodiment of the present invention may be prepared by providing a preformed film-coated tablet comprising a statin compound or statin compound in combination with at least one active ingredient. A first soft gelatin capsule shell part is then provided. The preformed film-coated tablet is introduced in the first soft gelatin capsule shell part. A second soft gelatin capsule shell part is provided. The first and second soft gelatin capsule shell parts are moved together at an end to form a cavity. At least one liquid phase is introduced into the cavity. Then the first and second soft gelatin capsule shell parts are sealed to form the soft gelatin capsule of the present invention.

Individual or multiple liquid phases may be introduced into the capsule by means of a single, dual or multiple wedge design that facilitates in-situ capsule filling of multiple phases.

The liquid fill phase may include different liquid phases which are layered side-by-side in the soft gelatin capsule. Each layered phase may incorporate an active ingredient or multiple active ingredients.

FIG. 1 illustrates soft gelatin capsules 140 of the present invention containing a solid round tablet 130. A preformed solid round tablet is also shown for comparison.

Soft gelatin capsules containing solid and liquid phases according to the invention provide a number of significant benefits for the administration of active ingredients.

The multi phase soft gelatin dosage form of the present invention can be used to deliver two or more active ingredients that otherwise would interact with each other. One or more active ingredients are dissolved in the liquid fill phase and the other active ingredient(s) in the solid dosage form.

Another use of the present invention is to provide effective control of the release of single or multiple APIs introduced in the solid dosage form and liquid phase. The liquid phase provides the capability of immediate release of the API in the liquid phase by virtue of a solution, pre-dispersed or self-emulsifying formulation. The solid phase may be coated to provide delayed release of the API in the solid phase.

When two or more capsules and or tablets are prescribed, their combination into one dosage form provides patient benefits and administration advantages of convenience and costs.

The present invention may be useful as a polypill. A polypill is a medication that contains a combination of active ingredients, reducing the number of tablets or capsules that need to be taken. Combined medications in the form of a polypill are useful for the treatment of cardiovascular disease and diabetes.

The present invention may reduce problems, such as time and expense, associated with combining two or more APIs into one dosage form. New combinations in one dosage form require development of new formulations and require pharmaceutical and clinical studies to demonstrate safety, efficacy and potency. The present invention provides the capability to incorporate more than one API into a unit dosage form utilizing established forms of the API or APIs that may be in liquid or solid phases. The present invention allows retention of the established tablet, caplet or capsule form of an API. This provides the capability to retain the pharmaceutical characteristics of the solid dosage form in combination with a liquid or fluid phase. Key characteristics include: physical and chemical stability, API release profile of the tablet or caplet, bioavailability and clinical performance. Retention of the established clinical performance by incorporation of the original solid may avoid the need to conduct extensive Phase III clinical studies that would otherwise be required with a new formulation.

By combining a number of established, off patent or generic medications, the present invention may be useful to treat cardiovascular conditions and provides the prospect of low cost treatment.

The present invention may be useful for the combined administration of unit doses of HMG-CoA inhibitors (statins) and Omega-3 fatty acids. The statins may be in the form of tablets or capsules containing single ingredient HMG-CoA inhibitors, or statins in combination with other active ingredients.

The present invention may permit the use of a smaller dosage form than those commercially sold. Encapsulation of a solid dosage form in a soft gelatin capsule provides protection against dissolution of the solid dosage form prior to reaching the intended target site. Thus, an encapsulated solid dosage form may not need to be as durable as compared to commercially available solid dosage forms. The present invention may reduce the need for excipients which function to prevent early dissolution of the solid dosage form when ingested, permitting the use of a smaller and cheaper solid dosage form.

The following are examples of the benefits of the present invention for the administration of combinations of medicines that may be in the form of a solid dosage form and liquid fill phase in a soft gelatin capsule.

EXAMPLES

Example 1

Preparation of Atorvastatin Calcium (Solid Dosage Form) & Omega 3 Oil (Liquid Phase)

A preformed film-coated tablet of atorvastatin calcium (commercially sold as LIPITOR® by Pfizer) is provided. A first soft gelatin capsule shell part is then provided. The preformed film-coated tablet is introduced in the first soft gelatin capsule shell part. A second soft gelatin capsule shell part is provided. The first and second soft gelatin capsule shell parts are moved together at an end to form a cavity. At least one liquid phase is introduced into the cavity. Then the first and second soft gelatin capsule shell parts are sealed to form the soft gelatin capsule of the present invention.

Example 2

Atorvastatin Calcium (Solid Dosage Form) & Omega 3 Oil (Liquid Phase)

A soft gelatin dosage form of the present invention may include the following composition:

| Ingredient | mg/soft gel |
| --- | --- |
| A. Solid Phase | |
| Film Coated Lipitor ® Atorvastatin Calcium Tablet (10 mg atorvastatin) | 152.8 |
| B. Liquid Phase | |
| High Potency Omega-3 Oil (37% DHA, 46% EPA) | 1000.00 |
| Total Fill Weight | 1091.30 |

Example 3

Atorvastatin Calcium (Solid Dosage Form) & Omega 3 Oil (Liquid Phase)

A soft gelatin dosage form of the present invention may include the following composition:

| Ingredient | mg/soft gel |
| --- | --- |
| A. Solid Phase | |
| Film Coated Lipitor ® Atorvastatin Calcium Tablet (10 mg atorvastatin) | 152.8 |
| B. Liquid Phase | |
| High Potency Omega-3 Oil (EPA (70% Ethyl Esters)) | 1000.00 |
| Total Fill Weight | 1091.30 |

Example 4

Rosuvastatin Calcium (Solid Dosage Form) & Omega 3 Oil (Liquid Phase)

A soft gelatin dosage form of the present invention may include the following composition:

| Ingredient | mg/soft gel |
| --- | --- |
| A. Solid Phase | |
| Film Coated Crestor ® Rosuvastatin Calcium Tablet (5 mg rosuvastatin) | 155.30 |
| B. Liquid Phase | |
| High Potency Omega-3 Oil (37% DHA, 46% EPA) | 1000.00 |
| Total Fill Weight | 155.30 |

Example 5

Comparative Stability Data

To illustrate how the soft gelatin dosage form of the present invention provides improved stability, the potency of atorvastatin in the soft gelatin dosage forms of the present invention as described in Examples 2 and 3 above, was compared relative to a commercial tablet of atorvastatin calcium (Lipitor®). In Example 2, a Lipitor® atorvastatin calcium tablet and high potency omega-3 oil (37% DHA & 46% EPA) were incorporated in a soft gelatin capsule. In Example 3, a Lipitor® atorvastatin calcium tablet and high potency omega-3 oil (EPA (70% Ethyl Esters)) were incorporated in a soft gelatin capsule.

The stability of the soft gelatin capsules were determined using gradient Ultra-High Performance Liquid Chromatography (UPLC) analysis with a Lipitor® atorvastatin calcium tablet standard reference. Samples of the soft gelatin dosage forms in Examples 2 and 3 above were tested under accelerating conditions for the intervals as described in the following table. The examples below demonstrate that the potency of Lipitor® atorvastatin calcium tablets incorporated in the dosage form of the present invention is stable over 6 months relative to a Lipitor® atorvastatin calcium tablet.

| | Relative Potency to Lipitor ® Tablet | |
| --- | --- | --- |
| Months on Storage at 40° C. | Lipitor ® Tablet in Omega-3 (DHA & EPA) | Lipitor ® Tablet in EPA (70% Ethyl Esters) |
| 0 | 100.05 | 100.05 |
| 1 | 100.22 | 100.16 |
| 2 | 100.30 | 100.34 |
| 3 | 100.23 | 99.73 |
| 6 | 100.28 | 100.09 |
| Linear Rate | 0.0282 | −0.0150 |

Example 6

Dissolution Data

The dissolution profile of five soft gelatin capsules of the fill composition described in Example 2 was determined using the USP dissolution apparatus #2 0.05M phosphate buffer, pH 6.8, at 37° C. as the dissolution medium with a paddle speed of 75 RPM.

The release of the drug was determined by UPLC using a UV detector at 245 nm.

The dissolution results are presented in the table below.

| TIME | % ATORVASTATIN | | | | |
|---|---|---|---|---|---|
| | 1 | 2 | 3 | 4 | 5 |
| 15 minutes | 0 | 2 | 4 | 2 | 60 |
| 30 minutes | 5 | 61 | 46 | 30 | 84 |
| 45 minutes | 47 | 82 | 60 | 62 | 101 |
| 60 minutes | 85 | 96 | 81 | 79 | 103 |
| 90 minutes | 98 | 98 | 100 | 103 | 104 |
| 120 minutes | 105 | 104 | 102 | 104 | 103 |

In view of the teachings presented herein, other modifications and variations of the present inventions will be readily apparent to those of skill in the art. The foregoing discussion and description are illustrative of some embodiments of the present invention, but are not meant to be limitations on the practice thereof.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. A multi phase soft gelatin oral capsule dosage form, comprising:
    a single preformed tablet comprising a statin compound consisting of rosuvastatin calcium, wherein the single preformed tablet has an established stability and bioavailability; and
    a liquid fill phase comprising about 1000 mg of omega-3 fatty acids consisting of an ethyl ester of eicosapentaenoic acid (EPA);
    wherein the preformed tablet is within the liquid fill phase, and
    wherein the liquid fill phase is within an oval soft gelatin capsule,
    wherein the size of the preformed tablet is less than a total internal volume of the soft gelatin capsule,
    wherein the preformed tablet has a hydroxy-propyl-methyl cellulose film coating,
    the multi phase soft gelatin oral capsule providing a stable rosuvastatin calcium stability profile when tested with Ultra-High Performance Liquid Chromatography (UPLC) analysis after storage at 40° C. for 6 months,
    wherein the multi phase soft gelatin oral capsule has equivalent rosuvastatin calcium bioavailability to the single preformed tablet, and
    wherein the multi phase soft gelatin oral capsule has a first soft gelatin capsule shell part and a second soft gelatin capsule shell part connected by a seal, wherein the preformed tablet is within the liquid fill phase within the total internal volume defined by the first soft gelatin capsule shell part and the second soft gelatin capsule shell part.

2. The soft gelatin oral capsule according to claim 1, wherein the liquid fill phase further comprises at least one additional active pharmaceutical ingredient.

3. The soft gelatin oral capsule according to claim 1, wherein the liquid fill phase further comprises at least one additional active ingredient selected from the group consisting of: an active pharmaceutical ingredient, nutraceutical, nutritional supplement, therapeutic substance, functional excipients and combinations thereof.

4. The soft gelatin oral capsule according to claim 1, wherein liquid fill phase further comprises diluent oils.

5. The soft gelatin oral capsule according to claim 1, the liquid fill phase further comprises vegetable oils, mineral oils, food grade oils, pharmaceutically acceptable oils or mixtures thereof.

6. The soft gelatin oral capsule according to claim 1, wherein the preformed solid dosage form has at least one coating selected from the group consisting of: film coating, gelatin coating, and combinations thereof.

7. The soft gelatin oral capsule according to claim 1, wherein the preformed tablet is a pharmaceutically finished tablet.

8. The soft gelatin oral capsule according to claim 1, wherein the preformed tablet comprises a moisture shield coating.

9. The soft gelatin oral capsule according to claim 1, wherein the preformed tablet and the liquid fill phase are independently introduced in the soft gelatin capsule.

10. The soft gelatin oral capsule according to claim 1, comprising rosuvastatin in amounts of 5 mg, 10 mg, 20 mg, 40 mg or 80 mg.

11. A multi phase soft gelatin oral capsule dosage form, comprising:
    a single preformed tablet comprising a statin compound consisting of rosuvastatin calcium, wherein the single preformed tablet has an established stability and bioavailability; and
    a liquid fill phase comprising about 1000 mg of omega-3 fatty acids consisting of an ethyl ester of eicosapentaenoic acid (EPA);
    wherein the preformed tablet is within the liquid fill phase, and
    wherein the liquid fill phase is within an oval soft gelatin capsule,
    wherein the size of the preformed tablet is less than a total internal volume of the soft gelatin capsule,
    wherein the preformed tablet has a hydroxyl-propyl-methyl cellulose film coating,
    the multi phase soft gelatin oral capsule dosage form providing a stable statin stability profile when tested with Ultra-High Performance Liquid Chromatography (UPLC) analysis after storage at 40° C. and 70% relative humidity for 6 months,
    wherein the multi phase soft gelatin oral capsule has equivalent statin bioavailability to the single preformed tablet, and
    wherein the multi phase soft gelatin oral capsule has a first soft gelatin capsule shell part and a second soft gelatin capsule shell part connected by a seal, wherein the preformed tablet is within the liquid fill phase within the total internal volume defined by the first soft gelatin capsule shell part and the second soft gelatin capsule shell part.

* * * * *